United States Patent [19]

Matzuk

[11] 4,246,792

[45] Jan. 27, 1981

[54] SELF-CONTAINED ULTRASONIC SCANNER

[76] Inventor: Terrance Matzuk, 154 Eileen Dr., Pittsburgh, Pa. 15214

[21] Appl. No.: 44,639

[22] Filed: Jun. 1, 1979

[51] Int. Cl.³ .......................................... G01N 29/00
[52] U.S. Cl. .................................................... 73/620
[58] Field of Search ................. 73/606, 607, 618, 620, 73/621, 627, 629, 644; 128/660; 367/7, 11; 358/112

[56] References Cited

U.S. PATENT DOCUMENTS

| | | | |
|---|---|---|---|
| 870,938 | 11/1907 | Cove | 310/36 |
| 3,406,564 | 10/1968 | Phillips et al. | 73/620 |
| 3,678,736 | 7/1972 | May | 73/634 |
| 3,690,311 | 12/1972 | Schorum et al. | 73/621 |
| 3,721,227 | 3/1973 | Larson et al. | 128/660 |
| 3,765,229 | 10/1973 | Spencer et al. | 73/640 |
| 3,784,805 | 1/1974 | Rolle | 367/11 |
| 3,789,833 | 2/1974 | Bom | 73/626 |
| 3,927,661 | 12/1975 | Takemura | 73/621 |
| 3,955,561 | 5/1976 | Eggleton | 73/621 |
| 3,974,826 | 8/1976 | Eggleton et al. | 73/621 |
| 3,990,300 | 11/1976 | Kossoff | 73/621 |
| 4,092,867 | 6/1978 | Matzuk | 73/609 |
| 4,200,885 | 4/1980 | Hofstein | 128/660 |

FOREIGN PATENT DOCUMENTS 461349  4/1975  U.S.S.R. .

OTHER PUBLICATIONS

W. H. Schuette et al., "Real Time Two Dimensional Mechanical Ultrasonic Sector Scanner with Electronic Control of Sector Width", Jul. 1976.

Primary Examiner—Stephen A. Kreitman
Attorney, Agent, or Firm—Arnold B. Silverman

[57] ABSTRACT

Self-contained ultrasonic scanning apparatus for insonifying a specimen including a housing, an ultrasonic transducer disposed within the housing and mounted for movement therewithin. Magnetic apparatus may be provided for effecting movement of the transducer and the magnetic apparatus may include a permanent magnet and an electromagnet. Apparatus is provided for electrically energizing the electromagnet. A cathode-ray tube is disposed within the housing with the screen visible from the exterior of the housing. Signal processing apparatus is provided for receiving signals from the transducer and suitably providing corresponding signals to the cathode-ray tube. The housing is preferably of such size and the apparatus of such weight as to be readily portable by an individual using a single hand.

62 Claims, 22 Drawing Figures

To Transducer

SELF-CONTAINED ULTRASONIC SCANNER

CROSS-REFERENCE TO RELATED PATENT

The present invention relates to several embodiments of a self-contained ultrasonic scanner and claims subject matter as to a portion of which the essential material constituting a disclosure of a preferred embodiment thereof is incorporated by reference herein from Matzuk U.S. Pat. No. 4,092,867 issued June 6, 1978 and entitled "Ultrasonic Scanning Apparatus."

BACKGROUND OF THE INVENTION

1. Field of the Invention

This invention relates to ultrasonic scanning apparatus and, more specifically it relates to self-contained, portable ultrasonic scanning apparatus.

2. Description of the Prior Art

The numerous advantages of the use of ultrasound in diagnostic medical procedures as well as other uses have long been known. In general, in connection with use on a human being or animal patient or other specimen, an ultrasonic wave is generated by a piece of ultrasonic testing equipment. The ultrasonic wave impinges upon the patient or other specimen and a number of reflected waves are sent back into the instrument. The signal is then converted into an electrical signal which may be visually displayed or recorded with intermediate processing to provide two dimensional information regarding the interior structure of the patient or other specimen.

One of the problems encountered with certain prior systems for certain uses is that the apparatus is relatively expensive and relatively immobile.

Another problem with prior known systems is that they are as a result of their size and weight, not readily portable, and therefore, not available throughout a medical institution or doctor's offices, but rather are generally confined to the radiology department.

There remains, therefore, a present need for a reliable, economically practical portable ultrasonic scanning system which is self-contained and yet produces images of acceptable quality.

SUMMARY OF THE INVENTION

The present invention has solved the above-described problems by providing a self-contained ultrasonic scanning apparatus for insonifying a specimen. The scanner has a housing, an ultrasonic transducer disposed within the housing and mounted for movement therewithin. Magnetic means are provided for effecting movement of the transducer with the magnetic means including both permanent magnet means and electromagnet means in a preferred embodiment. Energizing means are provided for electrically energizing the electromagnetic means and cathode-ray tube means are disposed within the housing with a screen visible from the exterior of the housing. Signal processing means for receiving signals from the transducer and delivering corresponding signals to the cathode-ray tube are provided.

The housing is sufficiently small and the apparatus sufficiently light weight as to be readily carried by the user.

In a preferred embodiment the apparatus may provide means for storing and dispensing acoustical gel. The electromagnetic means which energize the means for moving the transducer may also provide electromagnetic fields for use in controlling or deflecting the cathode-ray tube beam.

It is an object of the present invention to provide a self-contained ultrasonic scanner which is economical to manufacture and use.

It is a further object of this invention to provide such an ultrasonic scanner which is readily portable and may be transported and employed by the average individual using one hand.

It is another objective of this invention to provide such a scanner which has an energy source contained within it so as to not inhibit mobility of the apparatus.

It is also an object of the present invention to provide a miniaturized self-contained scanner which has simplified electrical circuitry as compared with conventional scanners.

It is a further object of this invention to provide such a scanner which has means for dispensing an acoustical gel therefrom.

These and other objects of this invention will be more fully understood from the following description of the invention on reference to the illustrations appended hereto.

BRIEF DESCRIPTION OF THE DRAWINGS

FIG. 11b is a fragmentary detail of a portion of the apparatus shown in FIG. 11a.

DESCRIPTION OF THE PREFERRED EMBODIMENTS

As used herein, the expressions "test specimen" or "specimen" will refer to various types of specimens to be examined or tested by ultrasonic means including, but not limited to, medical tests wherein portions of a human or animal body are tested ultrasonically. While for purposes of clarity of description, specific reference will be made to use in medical environments, it will be appreciated that other forms of test specimens may be subjected to testing by the apparatus of this invention in addition to the preferred medical use, and such other uses are expressly contemplated.

Figure 1:
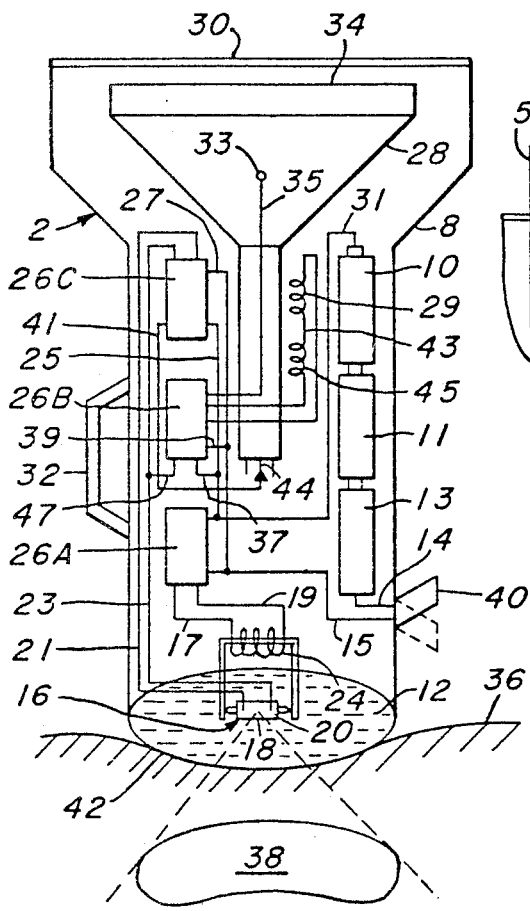
FIG. 1 is a partially schematic illustration of one form of the invention in contact with a specimen.

Referring now in greater detail to FIG. 1, there is shown a scanner 2 which has a sealed housing 8 which may be composed of any suitable material such as an electrical grade epoxy, for example. A suitable epoxy is that sold by Emerson Cummings under the name Stycast 2057. Batteries 10 which may advantageously be rechargeable nickel-cadmium c cells, for example, serve as the energizing means and are preferably disposed within the housing 8.

Figure 4:
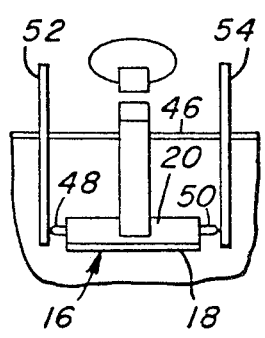
FIG. 4 is a schematic illustration of a portion of a preferred means for mounting the transducer for oscillatory movement.

Referring to FIGS. 1 and 4, a transducer assembly 16 (which consists of a transducer 18 and a permanent magnet 20 secured in overlying relationship with respect thereto) is provided within liquid-filled sealed compartment 12 at the lower end of the housing. Electromagnet 24 which is energized by batteries 10 serves to interact with the permanent magnet to establish oscillatory movement of the transducer assembly 16. The signals which return from the specimen being insonified are permitted to pass out of the sealed compartment 12 and into electronic processing means 26A, 26B, 26C from which they are presented to the cathode-ray tube 28. The cathode-ray tube screen 34 provides an image of the information obtained by the transducer 18. The image is visible through non-glare tinted lenticular viewing screen 30 which is a part of housing 8.

In a preferred embodiment shown in FIG. 1, batteries 10, 11, 13 supply power through switch 40 over electrically conductive leads 14, 15, 31. The electronic processing means 26A, 26B, 26C include frame rate oscillator 26A, deflection circuit and high voltage power supply 26B and receiver 26C. Leads 15, 31 connect the batteries 10, 11, 13 with frame rate oscillator 26A. Batteries 10, 11, 13 supply power to receiver 26C through leads 15, 27 and 31, 25, and also supply power to high voltage power supply 26B through leads 15, 27, 39 and 31, 25, 37. Electromagnet 24 is connected and energized by frame rate oscillator 26A by leads 17, 19. Electrical loop 43 is connected to high voltage power supply 26B and contains coils 29, 45 of cathode-ray tube to produce line and frame currents on coils 29, 45. This produces a scanning raster on cathode-ray tube 28 while providing high voltage to the cathode-ray tube 28 (by lead 35 at point 33) and producing the main bang pulse to transducer 10 (over leads 47, 23).

Leads 21, 23 deliver the electrical signal emerging from the transducer 18 to receiver 26C. The receiver 26C amplifies the echo signals from transducer 18 and converts the signals into video signals which are applied to cathode-ray tube 28 to modify brightness at points on the raster so as to display the ultrasonic image of organ 38. Lead 41 connects the receiver 26C with cathode-ray tube input 44.

In use, the scanner may be readily grasped and supported by handle 32 and turned on and off by switch 40. The lower surface of housing 8 is preferably composed of an acoustically transparent, semi-deformable or rigid diaphragm 42. In the form shown the specimen 36 is a portion of a human patient. The diaphragm 42 is urged into intimate contact with the patient 36 after a suitable acoustic gel layer has been provided therebetween. In this fashion, an internal organ 38 may be readily insonified by the oscillating transducer 18.

As it is a principal objective of the present invention to provide a system which may be established as a miniaturized portable system, in a preferred embodiment of the invention the overall length of the housing 8 will be about 7 to 11 inches, with 8 to 10 inches being the preferred size. Also, the preferred overall weight of the apparatus will be about 2 to 5 pounds with the preferred weight being about 3 to 4 pounds. The housing may advantageously be of a generally cylindrical configuration.

Referring now to FIG. 4, there is shown a preferred means of communicating the electrical signal emerging from the transducer 18 to the exterior of the liquid-filled compartment 12. The transducer assembly 16 is provided with a pair of generally diametrically opposed electrically conducted journal members 48, 50 which are in resiliently maintained pivotally supported contact with a pair of electrically conductive leaf spring pole members 52, 54 which extend upward through upper wall 46 of the liquid-filled compartment. Suitable electrical conductors (not shown) connect the poles 52, 54 with the electronic processing means 26.

Figure 2:
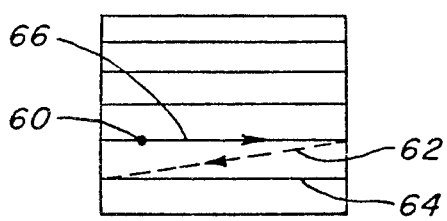
FIG. 2 illustrates schematically a television line deflection path.

Before turning to more structural features of the present invention, reference will be made to FIGS. 2 and 3 in order to discuss the concept of line deflection. In FIG. 2 there is shown a conventional television line deflection scan. In television systems the high-voltage pulse occurs when the scanning dot retraces as on line 62 from right to left to start a new scanning line 64. The original scanning line created by dot 60 is indicated by the reference number 66.

Figure 3:
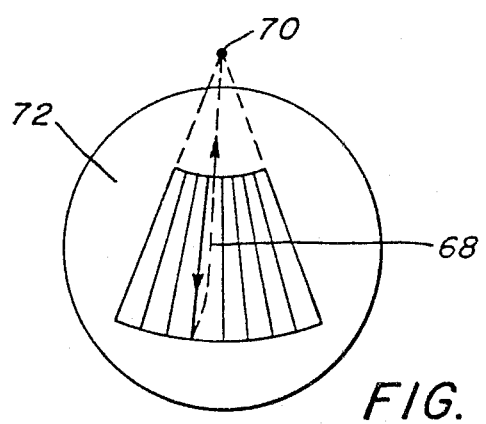
FIG. 3 illustrates schematically an ultrasound scan line deflection path.

In FIG. 3 there is shown a form of trapezoidal scan of the present invention. In this embodiment, the time access deflection is indicated as being oriented generally radially with respect to the virtual point 70. The retrace 68 to the virtual point 70 can be used to generate the high-voltage pulse to power the cathode-ray tube. The trapezoidal scan 72 may be started above the display area at virtual point 70. If the virtual point 70 is established, then the time the high voltage pulse occurs can be made to coincide with the desired time of the main bang pulse of the transducer. As a result, the design of the television line deflection circuits can be adapted to provide cathode-ray tube high voltage for ultrasound and also to provide the main bang transducer pulse.

Figure 5:
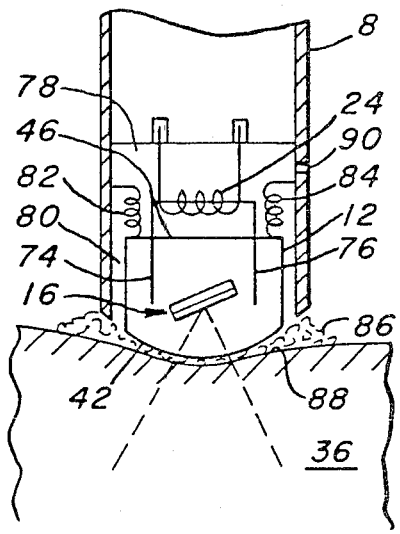
FIG. 5 is a schematic illustration of an embodiment of the invention adapted to dispense acoustical gel.

Referring now to FIG. 5 there is shown an embodiment of the invention which is adapted to store and dispense acoustical gel on the specimen. A suitable acoustical gel is that marketed by Parker Laboratories under the trade designation "Aquasonic 100". In this embodiment, the housing 8 is provided with the transducer assembly 16 which is secured within the sealed compartment 12. The electromagnet 24 cooperates with a pair of depending magnetically conductive poles 74, 76 which pass through the upper wall 46 of the sealed compartment 47. As is shown in this embodiment, the region overlying the upper wall 46 of the sealed compartment provides a reservoir 78 within which an acoustical gel is stored. The sealed compartment 47 in this embodiment has a substantially rigid upper wall 46 which permits it to serve as a piston in dispensing the acoustical gel provided in reservoir 78. An annular passageway 80 is provided between the periphery of the sealed compartment 47 and the interior surface of housing 8. This passageway provides communication between the reservoir 78 and the specimen 36. The passageway 80 is so sized as to resist discharge of acoustical gel with the compartment in its normal position. For example, the passageway may have a maximum transverse direction of about 0.3 to 0.5 inches. It is noted however, that the compartment is urged resiliently outwardly by means of compression springs 82, 84. When force is applied to membrane 42 so as to urge the sealed transducer containing compartment axially inwardly against the resistance of springs 82, 84 pressure is developed within the reservoir 78 which results in discharge of the gel 86 into the region of the upper surface 88 of the specimen 36.

It will be appreciated that in this embodiment of the scanner, as diaphragm wall 42 is urged into intimate contact with the specimen 36 this will cause the sealed compartment 47 to be urged axially inwardly against the resistance of springs 82, 84 to thereby establish pressure within reservoir 78 and cause the acoustical gel to be discharged through passageway 80 onto the surface of the specimen 88. Opening 90 which during use of the scanner may be closed by a suitable closure such as a plug, provides access to the reservoir 78 for refilling of the reservoir with acoustical gel. It will be appreciated that in some uses oils or surgically sterile lubricants may be substituted for the acoustical gel.

Figure 6:
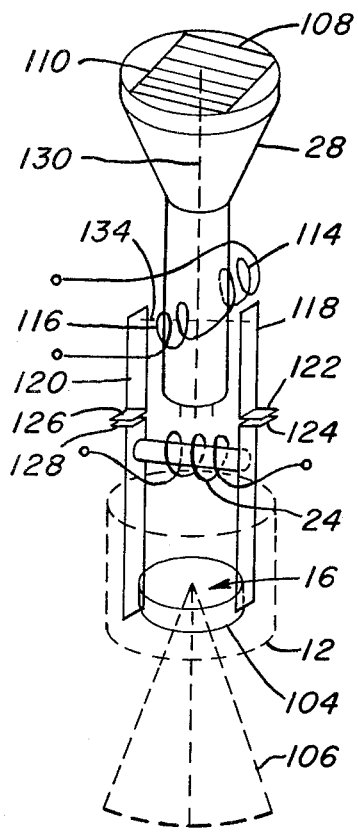
FIG. 6 is a schematic illustration of an embodiment of the invention wherein the magnetic field is employed to both oscillate the transducer and magnetically deflect the beam of the cathode-ray tube.

Referring now to FIG. 6, another embodiment of the invention will now be considered. In this embodiment there is effected an advantageous combination of the frame-deflection magnetic field applied to the cathode-ray tube with the magnetic field employed to operate the transducer assembly 16. Deflection coils 114, 116 deflect the beam 130 of the cathode-ray tube 28 along the line-deflection (time axis) direction 108. The electromagnet 24 which drives the transducer assembly 16 also provides the magnetic field to deflect the cathode-ray beam 130 in the frame direction 110. As the sealed compartment 12 and electromagnet 24 are removable, the magnetic field from the electromagnet 24 is coupled by means of shoes 122–124, 126–128 to pole piece extensions 118, 120 respectively to produce the extra magnetic field 134 needed in order to deflect the cathode-ray tube beam 130 along the frame deflection direction 110. In this manner, the need for separate frame deflection electrical components such as sweep generating circuits, power amplifier and additional deflection coils is eliminated.

Figure 7A:
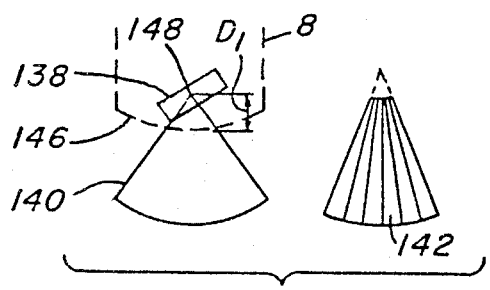
FIG. 7a illustrates a conventional ultrasonic raster scan.
Figure 7B:
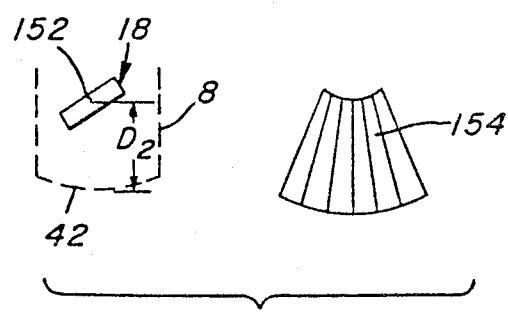
FIG. 7b illustrates a modified trapezoidal ultrasonic scan.

Referring now to FIG. 7(a), a conventional system wherein a transducer 148 provides a path of scan 140 which results in a sector scan 142 is shown. The distance $D_1$ between the lower housing wall 146 which would normally be in contact with the specimen and the center of transducer 140 generally indicated by $D_1$ is relatively small. In many conventional systems this distance may be in the order of 3 mm to 6 mm.

Figure 8A:
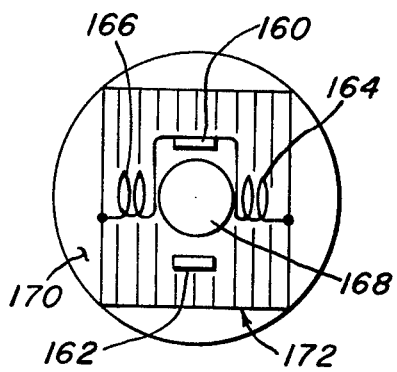
FIG. 8a illustrates traditional placement of a line deflection coil with respect to a cathode ray tube.

Referring now to the system of the present invention, the distance $D_2$ between the lower surface 42 of the housing 8 and the center 152 of the transducer 18 is substantially larger than $D_1$ and may preferably be on the order of 2 cm to 4 cm. This yields a desirable trapezoidal scan format rather than the sector scan. Referring now to FIG. 8(a) there is shown a pair of pole extensions 160, 162 disposed adjacent to the neck 168 of the cathode-ray tube with coils 164, 166 positioned generally diametrically opposed to each other. This arrangement results in the face of the cathode-ray tube 170 being provided with a rectangular raster 172.

Figure 8B:
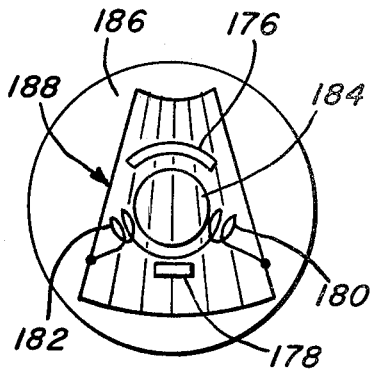
FIG. 8b illustrates a modified positioning of the line deflection coils in accordance with the present invention.

Referring now to FIG. 8(b), a suitable means for providing a trapezoidal raster on the cathode-ray tube screen will now be considered. In FIG. 8(a) there is shown a pair of pole extensions 160, 162 and a pair of coils 164, 166 positioned generally on diametrically opposed sides of the neck 168 of the cathode-ray tube. With this arrangement the face of the cathode-ray tube 170 is provided with rectangular raster 172.

Referring now to FIG. 8(b) the pole extension 176 is circumferentially substantially greater in extent than the pole extension 178. In a preferred form of the invention the circumferential extent of pole extensions 176 equals about 3 to 4 times the circumferential extent of pole extension 178 with respect to neck 184 of the cathode-ray tube. Also, the coils 180, 182 are not diametrically opposed, but rather are displaced such that lines drawn through the center of the coil from the center of the circle defined by the neck 184 of the cathode-ray tube 186 will have a smaller included angle of about 120 to 150 degrees. As is shown, this arrangement results in the screen of the cathode-ray tube 186 being provided with trapezoidal raster 188. All of this results from physical alteration of the geometry of the pole pieces 176, 178 and positioning of coils 180, 182.

Figure 9:
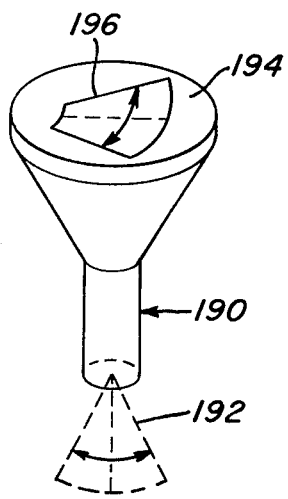
FIG. 9 illustrates schematically the positioning of the scan image as originally provided.
Figure 10:
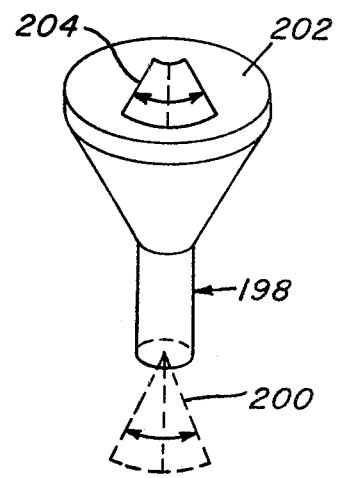
FIG. 10 illustrates schematically a modified orientation of the scan image.

Referring now to FIGS. 9 and 10, a further refinement of the invention will now be considered. FIG. 9 shows the orientation of the cathode-ray tube image as it would normally present the trapezoidal raster. The scanning plane 192 is so oriented with respect to the scanner 190 that the cathode-ray tube screen 194 will produce an imaging plane 196 having the orientation illustrated. While the method described in connection with FIG. 8 has produced the trapezoidal shape of the imaging raster, it may be desirable to displace this image by 90 degrees so that, as is shown in FIG. 10, the scanner 198 having a scanning plane 200 will show on the cathode-ray tube screen 202 an imaging plane having the orientation of plane 204.

Figure 11A:
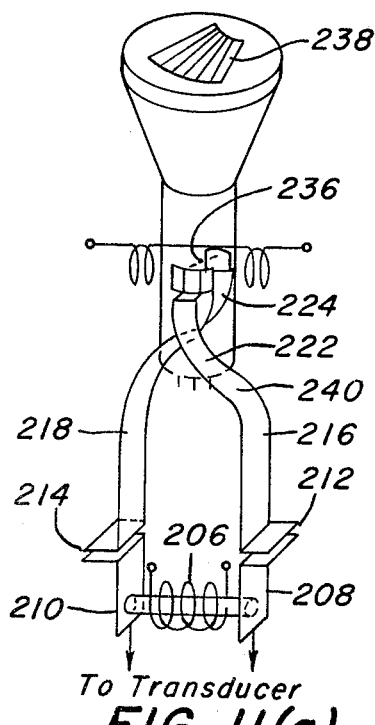
FIG. 11a illustrates a modified form of the apparatus adapted to produce the image orientation shown in FIG. 10.
Figure 11B:
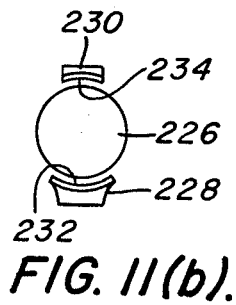

The desired right angle conversion may be readily accomplished by the apparatus shown in FIGS. 11(a) and 11(b).

As is shown in these figures, an electromagnet 206 cooperates with pole members 208, 210 which through pairs of shoes 212, 214 provide a magnetic field to the pole extensions which consist of a first pole extension having a lower portion 216 and an upper portion 222 and a second pole extension which has a lower portion 218 and an upper portion 224. It is noted that the lower portions 216, 218 are disposed in spaced generally parallel relationship with respect to each other and that each of the pole portions 216, 218 is oriented generally perpendicularly with respect to its corresponding upper portion 222, 224 as a result of a right angle twist in the pole extensions. In a preferred form, as illustrated, this serves to rotate the frame deflecting magnetic field 236 by 90 degress to correct the "right angle" orientation.

The complementary shapes of edges 232, 234 of flanges 228, 230 with respect to the neck 26 of the cathode-ray tube serve to facilitate contouring of the raster scan into the proper desired trapezoidal shape 238. The flanges 228, 230 serve to concentrate the magnetic field at the contoured extension tips in order to thereby reduce the tendency of regions 240, 242 to defocus the electrostatically focused cathode-ray tube beam.

For certain installations, it may be desirable to minimize the time factor which tends to result in the driving field of the electromagnet and hence the frame-deflection distance being slightly ahead of the physical motion of the transducer. If it is desired to minimize this time factor, several means of accomplishing this are shown in FIGS. 12, 13 and 14.

Figure 12:
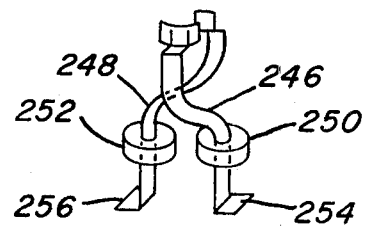
FIG. 12 illustrates a modified form of the apparatus incorporating eddy-current rings.

Referring now to FIG. 12, a pair of pole extensions 246, 248 which are twisted in the fashion shown in FIG. 11 are provided with a pair of shoe elements 254, 256. In order to alter the time in the desired direction a pair of copper eddy-current rings 250, 254 are provided around the lower portions of the extensions 246, 248, respectively. These eddy-current rings 250, 254 serve to short-circuit the magnetic fields from the pole piece extensions during the times of rapid flux changes to thereby accomplish electrically the equivalent of mechanical inertia at the oscillating transducer (not shown in this view).

Figure 13:
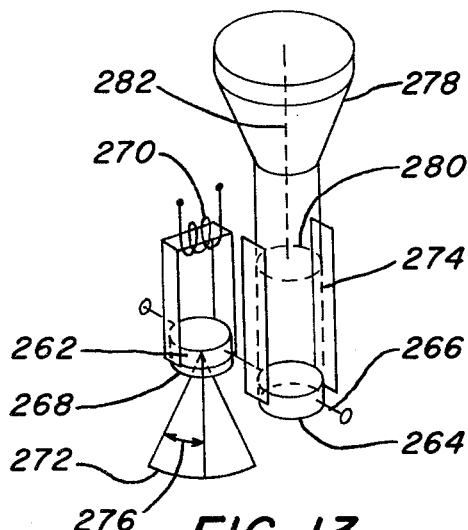
FIG. 13 illustrates a modified form of the apparatus employing a pair of oscillating permanent magnets.

In the system shown in FIG. 13 for minimizing consequences of the time differential, a pair of permanent magnets 262, 264 are connected by a shaft 266 so as to provide for relative coordinated movement. Magnet 266 moves under the influence of the magnetic field from electromagnet 270 and also is secured in overlying relationship with respect to transducer 268. The transducer 268 establishes the scan raster 272 within the specimen. Magnet 264 acts as a drone magnet which generates a field 274 in proportion to the angle 276 of the sector scan 272. Field 274 influences cathode-ray tube 278 in the region 280 in order to produce suitable framing-direction deflection of the beam 282.

Figure 14:
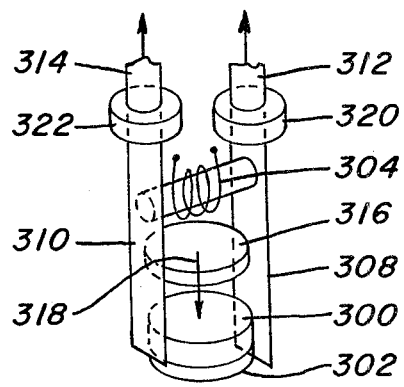
FIG. 14 illustrates a further modification of the apparatus employing a pair of permanent magnets.

Referring now to FIG. 14, a third means for minimizing the time differential is illustrated. This embodiment centers around the concept of simulating the effect of a return spring on a single oscillating permanent magnet-transducer assembly. As a result of the transducer mechanically resonating the time-shift differential can be reduced or eliminated. The oscillating permanent magnet 300 is secured in overlying relationship with respect to transducer 302 and the permanent magnet-transducer assembly are caused to oscillate under the magnetic field influence of electromagnet 304. Pole pieces 308, 310 lead to pole piece extensions 312, 314, respectively, in order to generate framing-deflection fields at the cathode-ray tube (not shown in this view). Fixed permanent magnet 316, however, exerts a "center return" force in the direction indicated by force arrow 318 which causes the oscillating permanent magnet 300 to elastically return to the neutral position. If the strengths of both permanent magnets 300, 316, their physical separation and sizes are properly proportioned, the oscillating magnet will operated preferentially at an angular frequency of $W^2 = K/I$ wherein W equals $2(pi)$ $(f)$. Pi is 3.14. The oscillating frequency $W = (pi)(f)$ where f is one half the frame scanning rate with K the torsional spring constant formed in part by second permanent magnet 316. I is the moment of inertia of the oscillating permanent magnet 300. When W/2 (pi) is provided to be one half the frame scanning frequency, the time shift distortion is minimized due to mechanical resonance. If desired, eddy-current rings 320, 322 may be added as a "trimming adjustment" to completely reduce the time-shift distortion problem.

Finally, one could actually employ a physical spring such as a sprial spring, if desired, however, this is not as preferable as the above-described solutions which have been illustrated in FIGS. 12 through 14 as the spring could contribute another area requiring periodic maintenance.

In the examples of circuits which follow, for purposes of clarity of illustration, certain specific numbers will be employed to establish various properties of the components and performance of the circuit. It will be appreciated, however, that these are merely examples and are not to be deemed as limiting on the invention.

Figure 15:
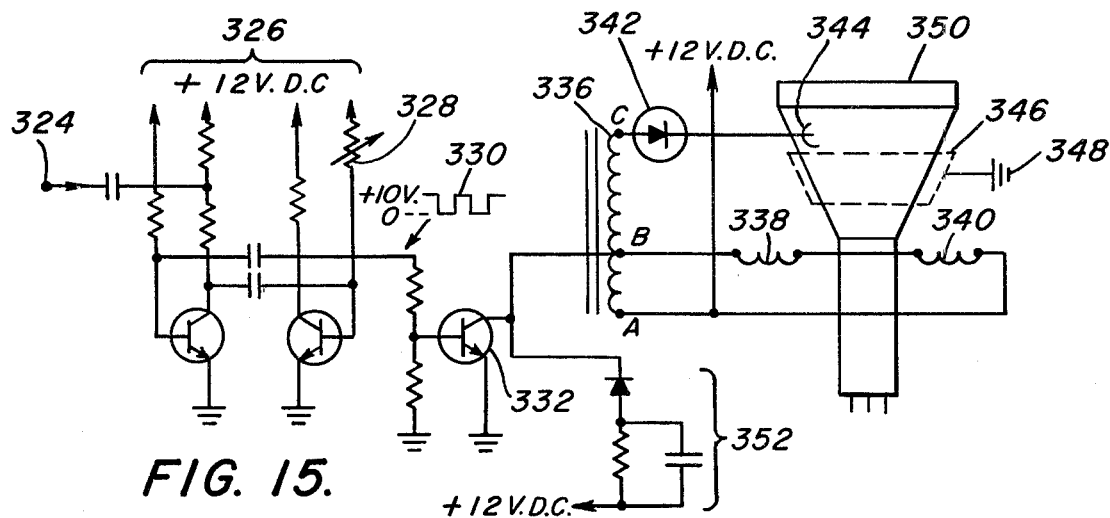
FIG. 15 illustrates a general circuit usable in the apparatus of the present invention.

FIG. 15 illustrates, in the context of a television set, a way of combining the high voltage power supply which is used to illuminate the cathode-ray tube with the line deflection (horizontal) circuitry. A typical line deflection television design is shown in FIG. 15. The horizontal synchronization pulses arrive at point 324 and cause multivibrator 326 to oscillate (pulse) at a frequency in step with the television picture signal being received. Horizontal hold control 328 allows multivibrator 326 to come within the desired frequency for synchronized oscillation. Multivibrator 326 may be of the "EcclesJordan" variety. The output signal 330 is a square wave. It turns the horizontal output transistor 332 on and off to thereby intermittently impress the full 12 volt battery power across terminal A and B of horizontal output transformer 336. During the conduction time of transistor 332, current gradually builds up according to the relationship $i = 1/L = $ *the integral from* $t_1$ *to* $t_2$ *of* $(e)(dt)$ in the line coil assembly 338, 340. L is the series (total) inductance of the coil assembly 338, 340, e is the applied 12 volts DC (battery power) and dt is the integration "on-time". The time $t_1 = 0$ microseconds and $t_2 =$ typically 54 microseconds. The maximum current at the end of 54 microseconds is about 0.5 ampere.

When the transistor 332 is turned off, as for example for about 9 microseconds, by multivibrator 326, this third current in the inductance 338, 340 acts as an energy source wherein the available energy is determined by: $w = \frac{1}{2} L i^2$ where W is the energy stored in 338, 340 at the end of the 54 microsecond interval, L is the inductance of coils 338, 340 and i is the current at the end of the scanning time. When the transistor 332 conducts, current builds up in the coils 338, 340 and the cathode-ray dot scans from left to right. When transistor 332 is turned off, the dot flies back to the left of the TV image and the energy W is available to discharge through transformer 336 to induce the high voltage pulse at point C of transformer 336.

As typical inductances of coils 338, 340 may be about 300 microhenries, with the energy available at the end of each horizontal scanning line being about 8 microjoules. As transistor 332, turns off, the energy discharge of coils 338, 340 impresses about 200 volts across terminals A and B of transformer 336 and due to the larger number of turns of wires between terminals B and C, the 200 volt pulse is magnified to perhaps about 6000 volts. Rectifier cartridge 342 converts this pulse to 6000 volts DC which is applied to the second anode connection 344 of the cathode-ray tube 350. An electrically conductive coating on the exterior 346 coating with ground connection 348 forms the filter capacitor to smooth out the 6000 volt DC applied at 344.

When transistor 332 begins to conduct (after the high voltage pulse) the damper diode-resistor capacitor combination at 352 conducts a portion of the energy build up current to prevent the secondary (terminals B and C) of transformer 336 from "ringing" with damped oscillations immediately after the high voltage pulse. The effect of damper-diode assembly 352 is to prevent distortion lines from appearing at the left of the image.

Among the preferred ways of adapting this television concept to the self-contained ultrasonic scanning apparatus of the present invention would be to combine the pulser to the transducer with the high-voltage rectifier cartridge 342 circuit. This provides a sharper pulse which is more concise in time. An alternate approach would be to replace the damper-diode assembly 352 with the transducer pulser circuit. This approach eliminates the damper circuit which elimination serves to reduce electrical losses. If the pulser circuit is designed to provide damping action and a pulse to the transducer then the line-deflection circuit operates at maximum efficiency with the lowest power consumption, but at the expense of a broader transducer pulse which is less concise in time.

Figure 16:
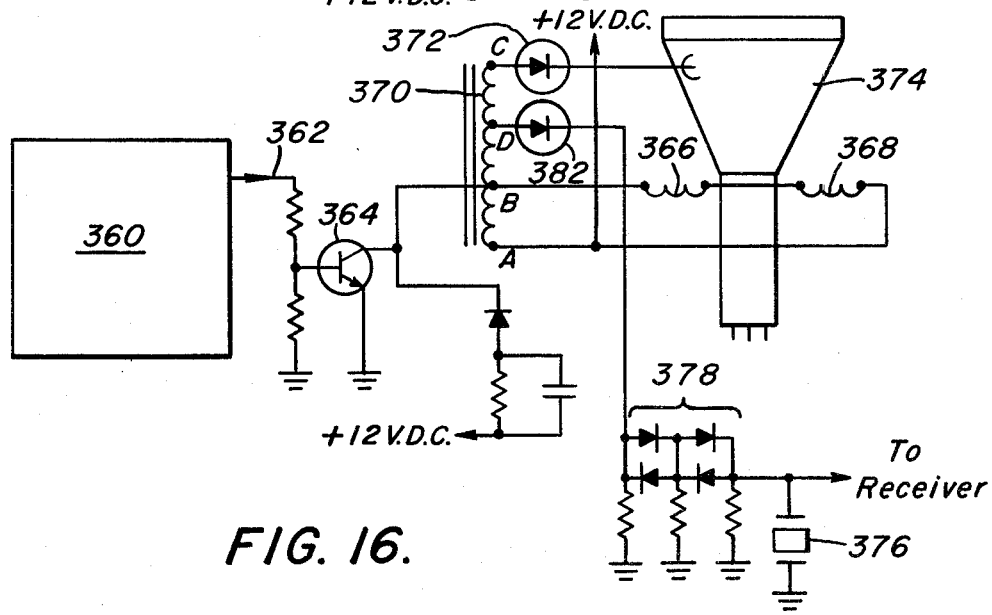
FIG. 16 is a modified form of the electrical circuit shown in FIG. 15.

Referring now to FIG. 16, there is shown a system wherein the pulser to the transducer is combined with the high voltage rectifier cartridge. A multivibrator 360 which may be similar in design to multivibrator 326 shown in FIG. 15 is proportioned to oscillate at about 3 KHz. The output at 362 that drives transistor 364 is proportioned to cause transistor 364 to conduct for about 300 microseconds and to turn off for about 30 microseconds. During the 300 microsecond period, current builds up in the line deflection coils 366, 368 and the cathode-ray tube dot scans from top to bottom of the trapezoidal scanning raster (not shown). When transistor 364 turns off, energy built up in coils 366, 368 discharges between terminals A and B of transformer 370 thereby inducing high voltage at C to operate rectifier 372 to light up cathode-ray tube 374. An additional tap D on transformer 370 provides a lower voltage pulse (about 800 volts peak) to pulse the "main bang" pulse of transducer 376. Transmit-receive circuit 378 isolates the lower voltages (approximately 1-3 volts) that leak through the reverse capacitance of diode 382 during scan time. Transmit-receive circuit 378 prevents interference from getting into the transducer 376 which listens to body deflections during the scan time. During retrace time, diode 382 conducts the 800 volt pulse through circuit 378 to transducer 376 at the same time rectifier 372 creates the high voltage (approximately 6000 volts) to illuminate cathode-ray tube 374.

Figure 17:
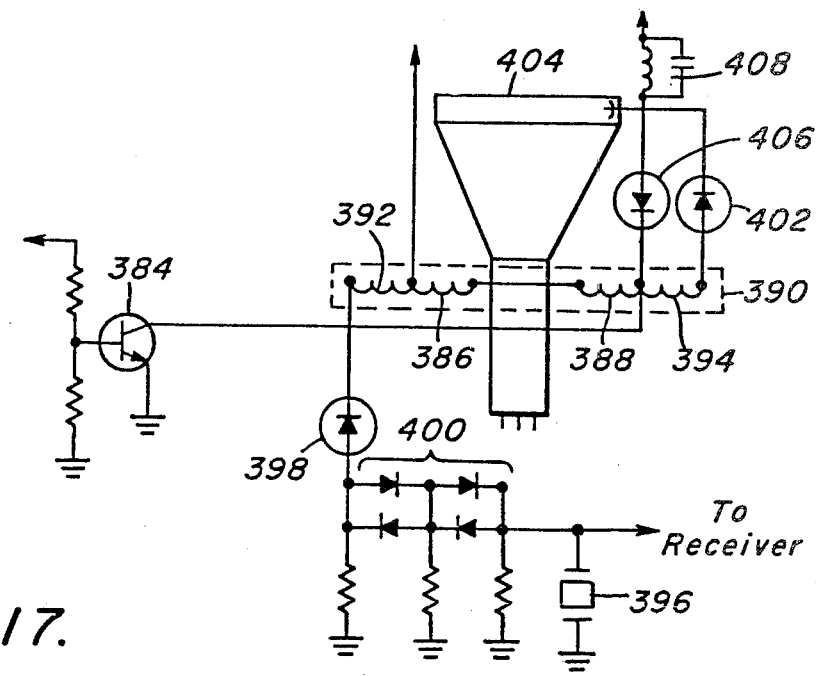
FIG. 17 is another modified form of electrical circuit for the apparatus.

Referring now to FIG. 17, a variation of the system shown in FIG. 16 involves combining the horizontal output transformer, the deflection coils and the high voltage and pulser power supplies into one set of coils and one circuit. Transistor 384 directly energizes inner coils 386, 388 of line deflection coil assembly 390. The pulser and high voltage windings are additional coils 392 and 394 wound directly adjacent to coils 386, 388 and undergo transformer action from magnetic fields of coils 386, 388. By suitably proportioning the wire size and the number of turns in coils 386, 388, 392, 394 one may obtain the desired 800 volt pulse from coil 392 and the desired 6000 volt pulse from coil 394. Coil 392 powers transducer 396 through pulser diode 398 and transmit-receive switch 400. Coil 394 operates rectifier cartridge 402 to provide high voltage to illuminate cathode-ray tube 404. Damper diode 406 and resistor-capacitor circuit 408 are still employed in a manner analogous to elements 352 of FIG. 15.

Referring still to FIG. 17, the alternate approach of eliminating the damper circuit, if the pulser diode 398 were reversed i.e. the horizontal line would underlie the triangular symbol which would be pointing directly downwardly, the electrical loading action of pulser circuit consisting of the reversed diode, transmit-receive switch 400 and the transducer 396 can substitute for the damping of circuit 406, 408 and components 406, 408 may be eliminated at substantial savings in power requirements e.g. on the order of about 1.5 to 2.5 watts.

Figure 18:
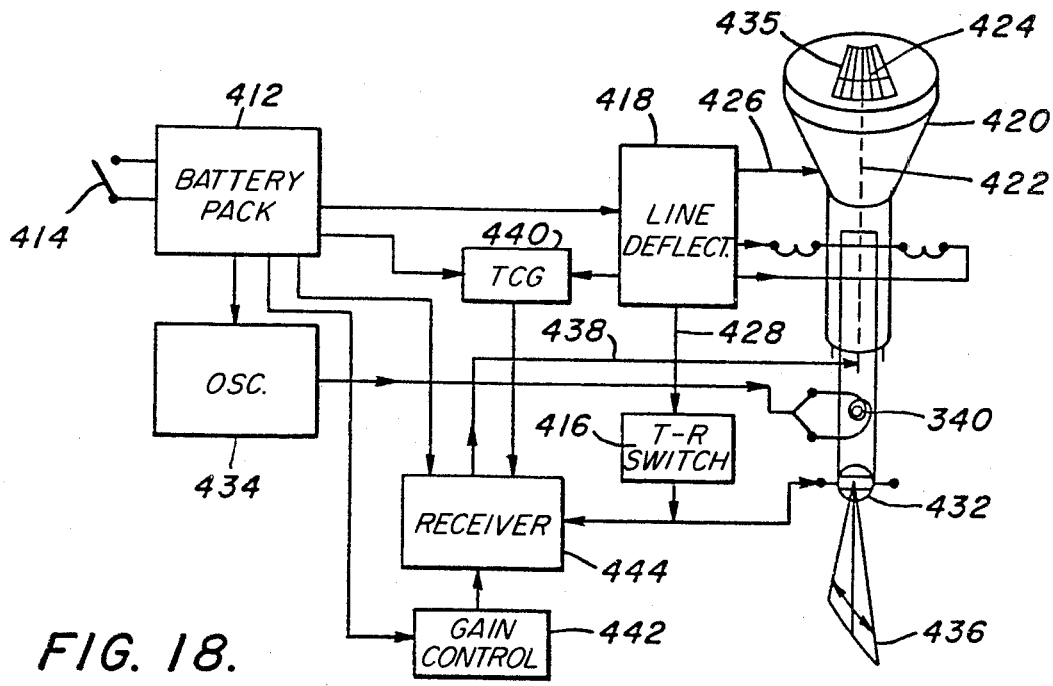
FIG. 18 is another form of circuit adapted for use in the apparatus of the present invention.

Referring now to FIG. 18, a general circuit arrangement for the self-contained scanner of the present invention is illustrated. Rechargeable battery pack 412 is activated by thumb operated slide switch 414 to power all circuits except the T-R switch 416. Application of DC power to the line-deflection circuit 418 activates the line 424 sweep deflection of cathode-ray tube beam 422. The same circuit 418 provides high voltage on lead 426 and pulse power on lead 428 to illuminate cathode-ray tube 420 and pulse transducer 432, respectively. DC power to frame rate oscillator 434 activates electromagnet 430 to mechanically oscillate transducer 432 and produce frame-deflection 435 on cathode-ray tube 420. Received reflections from body scan 436 are fed into the receiver 444 to produce video information on lead 438 in the form of variable brightness on the cathode-ray tube 420. Suitable time-controlled gain (TCG) ramp signals 440 are applied to receiver 444 to increase receiver sensitivity progressively as time elapses after each pulse. AGC (automatic gain control) circuit 442 automatically adjusts the average receiver gain in order that the external user controls are completely eliminated except for the of-on switch. Switch 414 could be built into the spring assembly 82, 84 (FIG. 5) which is associated with the displaceable sealed container 12. In this fashion the scanner would operate only when the compartment 12 is pressed onto a specimen. In the event that the switch is built into the spring tension in the scanner, the spring should be sufficiently great that the weight of the scanner alone would not turn on the scanner.

Figure 19:
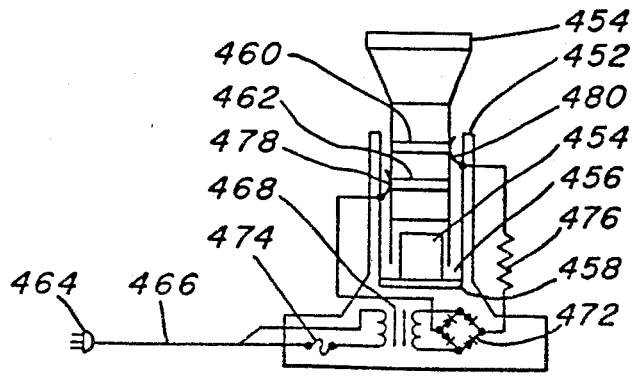
FIG. 19 illustrates a form of electrical charging stand for the apparatus of the present invention.

Referring to FIG. 19, an advantageous means of recharging the battery power system of the present invention is illustrated. A charging stand 452 is provided with a recess 456 which receives the scanner 454. A cushion 458 of the charging stand 452 supports the scanner 454. Two metal rings 460, 462 molded into the body of the scanner 454 accept DC charging current to recharge the internal batteries within the scanner. Alternating current main plug 464 and electrical line 466 admit AC power into reduction transformer 468 which in turn provides low voltage alternating current (on the order of about 18 volts AC) to power full-wave rectifier bridge 472. Rectifier 472 should preferably be of the full-wave variety in order to lessen the heating of transformer 468 and the resultant chances of blowing fuse 474. The output of rectifier 472 consists of unfiltered full-wave DC voltage on the order of approximately 20 volts DC, for example, and this voltage is applied through current limiting resistor 472 to energize clips 478, 480 that contact rings 460, 462 to thereby recharge the scanner 454. The transformer 468 is employed as both an isolation device and as a voltage reduction device to insure safety in the event that electrically conductive surgical tools fall into recess 456. The values of transformer 468, rectifier bridge 472, fuse 474 and resistor 476 should be so proportioned that a continuous short circuit neither overheats the charger nor blows fuse 474. Fuse 474 and the transformer 468, rectifier bridge 472 and resistor 476 should preferably be permanently potted into the stand and cord 466 and plug 464 should be molded together so that it is impossible to tamper with the charging stand 452. Charging stand 452 and the scanner are preferably designed to be completely immersible in water or isopropyl alcohol and also to be ethylene-oxide sterilizable.

It is preferred that the transformer 468 and resistor 476 be placed directly below the cushion 458 and that they be disposed within the casing material and thus electrically insulated from removable cushion 456. In this manner, heat from transformer 468 and resistor 476 warm the cushion and the transducer mechanism. This is desirable as a warm transducer requires less electromagnetic power than a cold transducer assembly. This is particularly preferable in order to avoid applying a cold assembly to the body of a human patient.

It will be appreciated that while certain preferred embodiments of the invention have been disclosed and illustrated herein, other variations will be apparent to those skilled in the art. For example, while a certain preferred housing configuration and size have been illustrated, other sizes and configurations may readily be employed advantageously while remaining within the scope of the present invention. Also, while in the preferred form the self-contained scanner has energizing means which are batteries housed within the unit, external sources of energy may be applied to the unit in addition to or in lieu of batteries. In addition, if desired, the battery pack could be replaced by a spring-wound generator suitable for use in a mobile emergency kit. It is also important to note that while certain preferred means for effecting transducer movement have been illustrated, other means of effecting movement relative to the housing may readily be employed while obtaining many of the benefits of the present invention.

While for convenience of reference herein certain directional words such as, "in" and "inwardly", "out" and "outwardly", and similar words of relative orientation have been employed, they are not to be deemed as limiting upon the invention in the absence of an express, specific indication to the contrary at a particular location.

Whereas, particular embodiments of the invention have been described above for purposes of illustration, it will be evident to those skilled in the art that numerous variations of the details may be made without departing from the invention as defined in the appended claims.

I claim:

1. Self-contained ultrasonic scanning apparatus for insonifying a specimen comprising
    a housing,
    an ultrasonic transducer disposed within said housing and mounted for movement therewithin,
    magnetic means for effecting movement of said transducer,
    energizing means for electrically energizing said magnetic means,
    cathode-ray tube means disposed within said housing with its screen visible from the exterior of said housing, and
    signal processing means for receiving signals from said transducer and delivering corresponding signals to said cathode-ray tube.

2. The ultrasonic scanning apparatus of claim 1 wherein
    said magnetic means includes permanent magnet means and electromagnet means.

3. The ultrasonic scanning apparatus of claim 2 wherein
    said magnetic means are disposed within said housing.

4. The ultrasonic scanning apparatus of claim 1 wherein
    said energizing means includes battery means.

5. The ultrasonic scanning apparatus of claim 4 wherein
    said battery means are disposed within said housing.

6. The ultrasonic scanning apparatus of claim 1 wherein
    said housing is sufficiently small and said apparatus is sufficiently light in weight as to be readily portable by an individual.

7. The ultrasonic scanning apparatus of claim 6 wherein
    said housing has a maximum length of about 7 to 11 inches and a maximum weight of about 2 to 5 pounds.

8. The ultrasonic scanning apparatus of claim 1 wherein
    an end of said housing adjacent to said transducer is composed of an acoustically transparent diaphragm.

9. The ultrasonic scanning apparatus of claim 8 wherein
    said transducer is disposed within a sealed liquid-containing compartment.

10. The ultrasonic scanning apparatus of claim 9 wherein
    said diaphragm provides a portion of said sealed compartment.

11. The ultrasonic scanning apparatus of claim 10 wherein
    said diaphragm is substantially rigid.

12. The ultrasonic scanning apparatus of claim 9 wherein
    said sealed-liquid containing compartment is mounted for relative axial movement with respect to the remaining portion of said apparatus.

13. The ultrasonic scanning apparatus of claim 12 wherein
    resilient means urge said compartment in a generally axially outwardly direction.

14. The ultrasonic scanning apparatus of claim 13 wherein
    said resilient means includes at least one compression spring.

15. The ultrasonic scanning apparatus of claim 13 including reservoir means disposed within said housing for receiving and dispensing a supply of acoustical gel, and
    passageway means in communication with said reservoir means and the exterior of said housing, whereby said apparatus will act as a source of acoustical gel which is dispensed onto said specimen.

16. The ultrasonic scanning apparatus of claim 15 wherein
    an inner portion of said compartment is disposed adjacent to said reservoir, whereby movement of said compartment axially inwardly against the force of said resilient means will urge a portion of said gel outwardly through said passageway means.

17. The ultrasonic scanning apparatus of claim 15 including
access means for permitting communication between said reservoir and the exterior of said housing for permitting filling of said reservoir.

18. The ultrasonic scanning apparatus of claim 16 wherein
said passageway means is disposed between said compartment and said housing, and
said passageway means being of sufficiently small size as to resist discharge of said gel in the absence of axially inward pressure applied to said compartment.

19. The ultrasonic scanning apparatus of claim 2 wherein
said permanent magnet means are mounted on said transducer, and
said electromagnet means having a pair of spaced poles extending into said compartment and positioned on opposite sides of said transducer.

20. The ultrasonic scanning apparatus of claim 19 wherein
said poles have upper portions extending out of said compartment,
electrical coil means operatively associated with said upper portions, and
said energizing means energizing said coil means, whereby said electromagnetic poles will cooperate with said permanent magnet means to effect oscillation of said transducer.

21. The ultrasonic scanning apparatus of claim 19 including
journal means operatively associated with said transducer for pivotally mounting said transducer, and
electrically conductive leaf spring means in contact with said journal means for energizing said transducer and for delivering transducer output signals to said signal processing means.

22. The ultrasonic scanning apparatus of claim 19 wherein
said spaced poles extend upwardly to a position adjacent said cathode-ray tube, whereby said upper extensions of said poles provide means for deflecting the cathode-ray tube beam.

23. The ultrasonic scanning apparatus of claim 22 including
shoe means cooperating with said pole extensions to couple said electromagnetic means with said pole extensions, and
upper coil means cooperating with said pole extensions for deflecting said cathode-ray tube beam.

24. The ultrasonic scanning apparatus of claim 1 wherein
said axially outermost portion of said compartment being spaced about 2 cm to 4 cm from the center of said transducer.

25. The ultrasonic scanning apparatus of claim 23 wherein
said upper coil means are positioned so as to provide a substantially trapezoidal raster.

26. The ultrasonic scanning apparatus of claim 23 wherein
said upper coil means have two coil sections positioned around the cathode-ray tube circumference adjacent points on the cathode-ray tube circumference forming a smaller included angle of about 120° to 150° degrees.

27. The ultrasonic scanning apparatus of claim 26 wherein
the upper extension of said poles are deformed so as to provide portions disposed generally in a plane perpendicular to the lower portion of said poles.

28. The ultrasonic scanning apparatus of claim 27 wherein
said upper extensions are bent generally inwardly, whereby spaced pole portions in the upper extensions will be closer to each other than the corresponding spacing between lower portions of said poles.

29. The ultrasonic scanning apparatus of claim 27 wherein
said upper pole extensions have means for concentrating the magnetic field to reduce the tendency of the cathode-ray tube beam to defocus.

30. The ultrasonic scanning apparatus of claim 29 wherein
said concentrating means include dissimilar arcuate pole piece extensions disposed in close proximity to the neck of said cathode-ray tube.

31. The ultrasonic scanning apparatus of claim 30 wherein
a pair of said arcuate pole piece extensions are disposed on opposite sides of said neck.

32. The ultrasonic scanning apparatus of claim 31 wherein
one said arcuate pole piece extension has a circumferential extent of about three to four times the circumferential extent of the other said arcuate pole piece.

33. The ultrasonic scanning apparatus of claim 28 wherein
eddy-current rings are disposed around each said upper extension for short circuiting the magnetic fields from said upper extensions during rapid flux changes.

34. The ultrasonic scanning apparatus of claim 1 wherein
said permanent magnet means includes a first permanent magnet and a second permanent magnet,
the first said permanent magnet being operatively associated with said transducer to establish oscillation thereof,
shaft means connecting said first and said second permanent magnet means,
said second permanent magnet means being disposed closer to said cathode-ray tube than said first permanent magnet means, whereby oscillation of said transducer by said first permanent magnet means will cause responsive movement of said second permanent magnet means and alter the position of the magnetic field generated by said second permanent magnet means.

35. The ultrasonic scanning apparatus of claim 22 wherein
said permanent magnet means includes a first permanent magnet and a second permanent magnet,
the first said permanent magnet being operatively associated with said transducer to establish oscillation thereof, and
said second permanent magnet means being interposed between said first permanent magnet means and said electromagnet means.

36. The ultrasonic scanning apparatus of claim 13 including
   switch means operatively associated with said energizing means for turning said scanner on and off, and
   said switch means being in an off position when said resilient means are in a substantially uncompressed state and being in an on position when said resilient means are at least partially compressed.

37. The ultrasonic scanning apparatus of claim 1 wherein
   a portion of the lower surface of said housing underlying said transducer being spaced about 2 cm to 4 cm from the center of said transducer.

38. The ultrasonic scanning apparatus of claim 7 wherein
   said housing has a generally cylindrical shape.

39. The ultrasonic scanning apparatus of claim 38 wherein
   the portion of said housing adjacent to said cathode-ray tube screen having a larger diameter than the portion of said housing adjacent said transducer.

40. The ultrasonic scanning apparatus of claim 1 wherein
   said signal processing means includes receiver means for converting echo signals from said transducer into video signals.

41. The ultrasonic scanning apparatus of claim 40 wherein
   said magnetic means includes permanent magnet means and electromagnet means, and
   said energizing means including frame rate oscillator means for energizing said electromagnet.

42. The ultrasonic scanning apparatus of claim 41 including
   deflection circuit and high voltage power supply means for energizing deflecting coils of said cathode-ray tube, and
   the high voltage portion of the cathode-ray tube and said transducer.

43. The ultrasonic scanning apparatus of claim 42 wherein
   said energizing means energize said deflection circuit and high voltage power supply means, and
   said energizing means energize said frame rate oscillator means.

44. The ultrasonic scanning apparatus of claim 43 wherein
   said energizing means include battery means.

45. The ultrasonic scanning apparatus of claim 44 wherein
   first electrical lead means connect said battery means with said receiver means, said frame rate oscillator means and said deflection circuit and high voltage power supply means.

46. The ultrasonic scanning apparatus of claim 45 wherein
   second electrical lead means connect said frame rate oscillator means with said electromagnet means.

47. The ultrasonic scanning apparatus of claim 46 wherein
   third electrical lead means connect said deflection current and high voltage power means with the deflection coils of said cathode-ray tube,
   fourth electrical lead means connect said deflection current and high voltage power means with said high voltage input of said cathode-ray tube for illuminating said cathode-ray tube.

48. The ultrasonic scanning apparatus of claim 47 wherein
   fifth electrical lead means connect said receiver means with said transducer.

49. The ultrasonic scanning apparatus of claim 48 wherein
   sixth electrical lead means connect said deflection current and high voltage power supply means directly or indirectly with said transducer for energizing said transducer.

50. The ultrasonic scanning apparatus of claim 1 including
   circuit means for energizing the high voltage portion of said cathode-ray tube, the line deflection circuitry and the transducer pulser circuitry,
   said circuit means including multivibrator means and transistor means operating responsively to receipt of output from said multivibrator,
   said circuit means having transformer means operatively associated with said transistor for delivering current to the deflection coils of said cathode-ray tube when said transistor means is on and permitting discharge of said coils through said transformer means to the cathode-ray tube high voltage input, and
   said transformer means providing voltage pulses to said transducer.

51. The ultrasonic scanning apparatus of claim 50 wherein
   first and second electrical conductor means connect said coils with said transformer means,
   third electrical conductor means connect said cathode-ray tube high voltage input with said transformer means, and
   fourth electrical conductor means connect said transducer with said transformer means.

52. The ultrasonic scanning apparatus of claim 51 wherein
   first rectifier means are operatively associated with said third electrical conductor means, and
   second rectifier means are operatively associated with said fourth electrical conductor means.

53. The ultrasonic scanning apparatus of claim 52 wherein
   transmit receive circuit means are operatively associated with said fourth electrical conductor means for resisting entry of interference into said transducer.

54. The ultrasonic scanning apparatus of claim 1 including
   circuit means for energizing the high voltage portion of said cathode-ray tube, the line deflection circuitry and the transducer pulser circuitry,
   said circuit means including transistor means operatively associated with a pair of cathode-ray tube deflection coils, a high voltage coil and a transducer pulser coil,
   said coils being so positioned relative to each other and so connected to said transistor that said high voltage coil and said transducer pulser coil undergo transformer action resulting from the magnetic fields from said deflection coils.

55. The ultrasonic scanning apparatus of claim 54 including
   first electrically conductive means connecting said transducer pulser coil with said transducer, and
   rectifier means operatively associated with said first electrically conductive means.

56. The ultrasonic scanning apparatus of claim 55 including transmit-receive circuit means operatively associated with said first electrically conductive means.

57. The ultrasonic scanning apparatus of claim 56 including second electrically conductive means connecting said high voltage coil and said high voltage input of said cathode-ray tube, and rectifier means operatively associated with said second electrically conductive means.

58. The ultrasonic scanning apparatus of claim 1 wherein said energizing means include rechargeable battery means, and electrically conductive means permitting electrical conduction between said batteries and the exterior of said housing.

59. The ultrasonic scanning apparatus of claim 58 wherein said electrically conductive means include a pair of electrically conductive members secured to the exterior of said housing and means electrically connecting said members to said batteries.

60. The ultrasonic scanning apparatus of claim 58 including scanner recharging means operatively associated with said scanner, said recharging means having a recess within which at least a portion of said scanner is received, electrical contacts within said recess for contacting said scanner electrically conductive means, and said recharging means having power supply means for energizing said recharging means.

61. The ultrasonic scanning apparatus of claim 60 wherein said power supply means include transformer means, rectifier means and resistor means.

62. The ultrasonic scanning apparatus of claim 61 wherein at least one of said resistor means and said transformer means disposed in generally underlying relationship with respect to the base of said recess.

* * * * *

UNITED STATES PATENT AND TRADEMARK OFFICE
CERTIFICATE OF CORRECTION

PATENT NO. : 4,246,792

DATED : January 27, 1981

INVENTOR(S) : Terrance Matzuk

It is certified that error appears in the above-identified patent and that said Letters Patent are hereby corrected as shown below:

Column 7, line 2, change "26" to --226--.

Column 7, line 63, change "W = (pi)(f)" to --W = 2(pi)(f)--.

Column 8, line 6, change "sprial" to --spiral--.

Signed and Sealed this

Seventh Day of July 1981

[SEAL]

Attest:

RENE D. TEGTMEYER

Attesting Officer     Acting Commissioner of Patents and Trademarks